United States Patent
Kim et al.

(10) Patent No.: US 9,220,426 B2
(45) Date of Patent: Dec. 29, 2015

(54) NEURAL TUBE FOR RECOVERING FUNCTION OF INJURED NERVE

(71) Applicant: KOREA INSTITUTE OF SCIENCE AND TECHNOLOGY, Seoul (KR)

(72) Inventors: Jinseok Kim, Seoul (KR); Jinwoo Jeong, Seoul (KR); Jun-Kyo Francis Suh, Seoul (KR); Kuiwon Choi, Seoul (KR); Inchan Youn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 142 days.

(21) Appl. No.: 14/080,282

(22) Filed: Nov. 14, 2013

(65) Prior Publication Data

US 2014/0163348 A1    Jun. 12, 2014

(30) Foreign Application Priority Data

Dec. 7, 2012  (KR) .................. 10-2012-0142266

(51) Int. Cl.
*A61B 5/04* (2006.01)
*A61N 1/05* (2006.01)

(52) U.S. Cl.
CPC .......... *A61B 5/04001* (2013.01); *A61N 1/0551* (2013.01)

(58) Field of Classification Search
CPC ................................................ A61B 5/04001
USPC ......................................... 600/377; 607/116
See application file for complete search history.

(56) References Cited

U.S. PATENT DOCUMENTS

| | | | |
|---|---|---|---|
| 8,666,499 B2* | 3/2014 | Youn et al. | 607/50 |
| 8,676,334 B2* | 3/2014 | Youn et al. | 607/48 |
| 2002/0051806 A1 | 5/2002 | Mallapragada et al. | |
| 2008/0228240 A1* | 9/2008 | Edell et al. | 607/48 |
| 2011/0251473 A1* | 10/2011 | Moran et al. | 600/373 |
| 2012/0259388 A1* | 10/2012 | Galvan-Garcia | 607/62 |

FOREIGN PATENT DOCUMENTS

| | | |
|---|---|---|
| KR | 2002-0029069 A | 4/2002 |
| KR | 10-2011-0005501 A | 1/2011 |
| KR | 10-2012-0110231 A | 10/2012 |

OTHER PUBLICATIONS

Stieglitz, T., et al. "A biohybrid system to interface peripheral nerves after traumatic lesions: design of a high channel sieve electrode." Biosensors and Bioelectronics 17.8 (2002): 685-696.

(Continued)

*Primary Examiner* — Lee S Cohen
(74) *Attorney, Agent, or Firm* — NSIP Law

(57) ABSTRACT

A neural tube capable of complexly playing roles of a support for regenerating a nerve and a nerve electrode has a support connected to a terminal of an injured nerve, and a sieve electrode having an electrode hole formed in a body thereof and a circular electrode formed around the electrode hole, wherein the body of the sieve electrode is buried in the support, wherein a cavity-type channel is formed at the support to extend to the inside of the support, wherein the electrode hole is aligned with the channel, and wherein a nerve cell growing along the channel at the terminal of the injured nerve is capable of contacting the circular electrode.

8 Claims, 7 Drawing Sheets

(56) References Cited

OTHER PUBLICATIONS

Lacour, Stéphanie P., et al. "Long micro-channel electrode arrays: a novel type of regenerative peripheral nerve interface." Neural Systems and Rehabilitation Engineering, IEEE Transactions on 17.5 (2009): 454-460.

Gros, Thomas, et al. "Regeneration of long-tract axons through sites of spinal cord injury using templated agarose scaffolds." Biomaterials 31.26 (2010): 6719-6729.

* cited by examiner

NEURAL TUBE FOR RECOVERING FUNCTION OF INJURED NERVE

CROSS-REFERENCE TO RELATED APPLICATION

This application claims priority to Korean Patent Application No. 10-2012-0142266, filed on Dec. 7, 2012, and all the benefits accruing therefrom under 35 U.S.C. §119, the contents of which in its entirety are herein incorporated by reference.

BACKGROUND

1. Field

The present disclosure relates to a neural tube, and more particularly, to a neural tube connected to an injured nerve to effectively recover a function of the nerve.

2. Description of Related Art

If a nerve is damaged by cutting or the like, a stimulation occurring in or out of a living body is not properly transferred, which gives a bad influence to an organism. Therefore, endeavors for recovering a function of the injured nerve are being made from various angles.

In order to recover a function of an injured nerve, a support may be inserted between the cut nerve strands to physically fix the cut nerve strands, and the nerve is regenerated in the support so that the cut nerve strands are connected again.

However, since there is a limit in a nerve regeneration length, if a nerve is cut and a predetermined length of the nerve is lost, it is very difficult to regenerate the nerve as much as the cut nerve strands contact each other.

In addition, even though the nerve is regenerated so that the cut nerve strands are connected to each other, it is very difficult to normally recover the original nerve function. For example, a nerve strand which should extend from the brain to the arm may be erroneously connected to a nerve strand connected to the leg. In this case, the nerve system may be confused, which may give rather a bad influence on the living body.

Therefore, from understanding a function of a nerve that electrically exchanges signals, an effort for supplementing a nerve function by collecting electric signals of a nerve through an electrode is being made.

However, according to this technique, an electrode is attached directly to a cut nerve and thus is not firmly supported, and it is impossible to figure out a regeneration state of the nerve according to medicine or stimulation treatment.

In addition, since an electrode is directly attached to a nerve, the nerve tissues may be physically damaged.

SUMMARY

The present disclosure is directed to providing a neural tube which may complexly play roles of a support for regenerating a nerve and a nerve electrode, and a neural signal detection device having the same.

In one aspect, there is provided a neural tube, which includes: a support connected to a terminal of an injured nerve; and a sieve electrode having an electrode hole formed in a body thereof and a circular electrode formed around the electrode hole, wherein the body of the sieve electrode is buried in the support, wherein a cavity-type channel is formed at the support to extend to the inside of the support, wherein the electrode hole is aligned with the channel, and wherein a nerve cell growing along the channel at the terminal of the injured nerve is capable of contacting the circular electrode.

According to an embodiment, a plurality of electrode holes may be formed in the sieve electrode, a plurality of channels may be formed in the support, and the electrode holes may be aligned with the channels in a one-to-one relation.

In addition, the sieve electrode may be disposed perpendicular to the length direction of the channel, and the center of the electrode hole may be located on a longitudinal axis of the channel.

In addition, the support may have a cylindrical shape or a semicylindrical shape.

In addition, the support may be made of hydrogel.

In addition, the channel may contain a medicine for assisting regeneration of the nerve cell or reducing an immune reaction.

In addition, the sieve electrode may include an electrode connector extending from a circular or semicircular electrode body to the outside of the support, and a linear electrode electrically connected to the circular electrode may be formed at the electrode connector.

The neural tube according to the present disclosure may simultaneously play a role of a support for regenerating an injured nerve and a role of a nerve electrode for detecting a neural signal. In addition, nerve cells are firmly supported in a channel.

If a neural signal detection device is configured by using such a neural tube, a neural signal may be properly sent or received without generating a nerve and directly contacting nerve strands. Therefore, errors of the nerve system may be minimized, and there is no limit in a nerve regeneration length.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
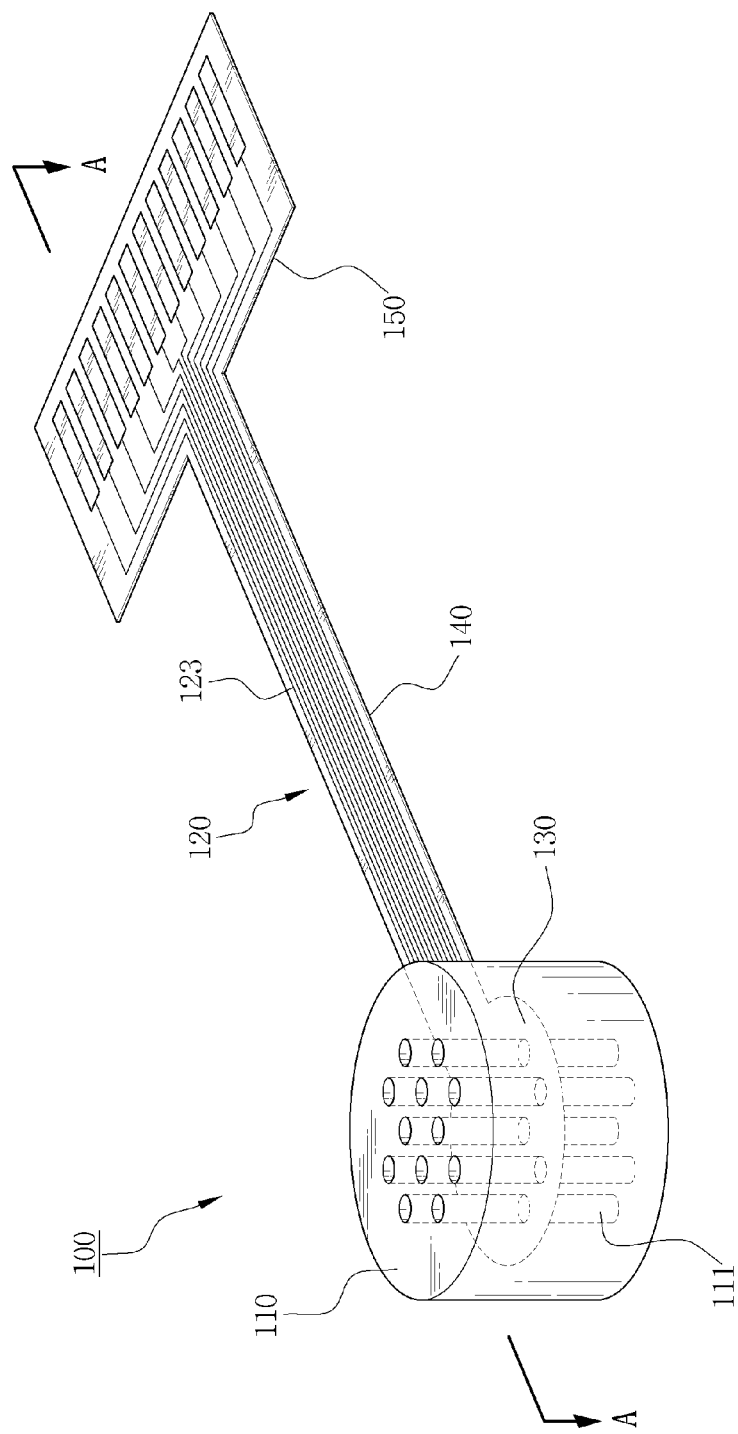
FIGS. 1 to 3 show a neural tube according to an embodiment of the present disclosure.

Hereinafter, an embodiment of the present disclosure will be described with reference to the accompanying drawings. Even though the present disclosure is based on the embodiments depicted in the drawings, it is just for better understanding, and the spirit, essential configurations and operations of the present disclosure are not limited thereto.

Figure 2:
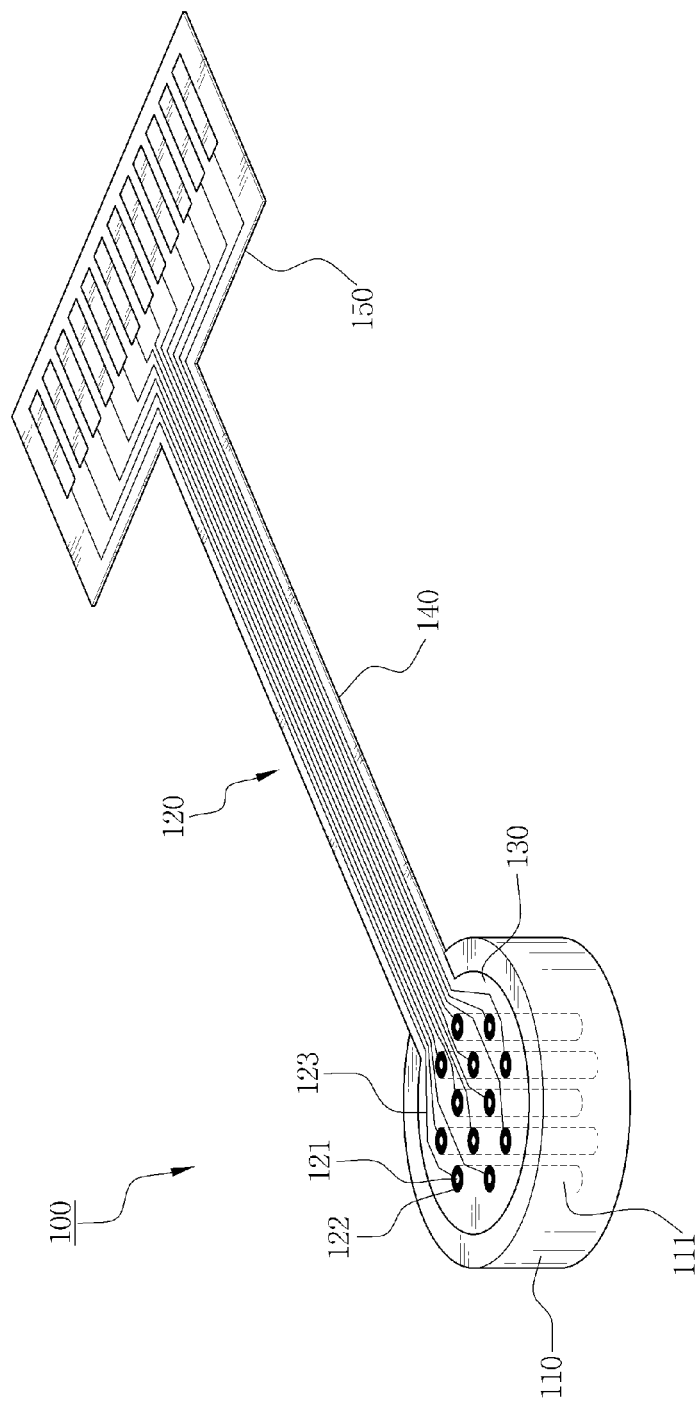
Figure 3:
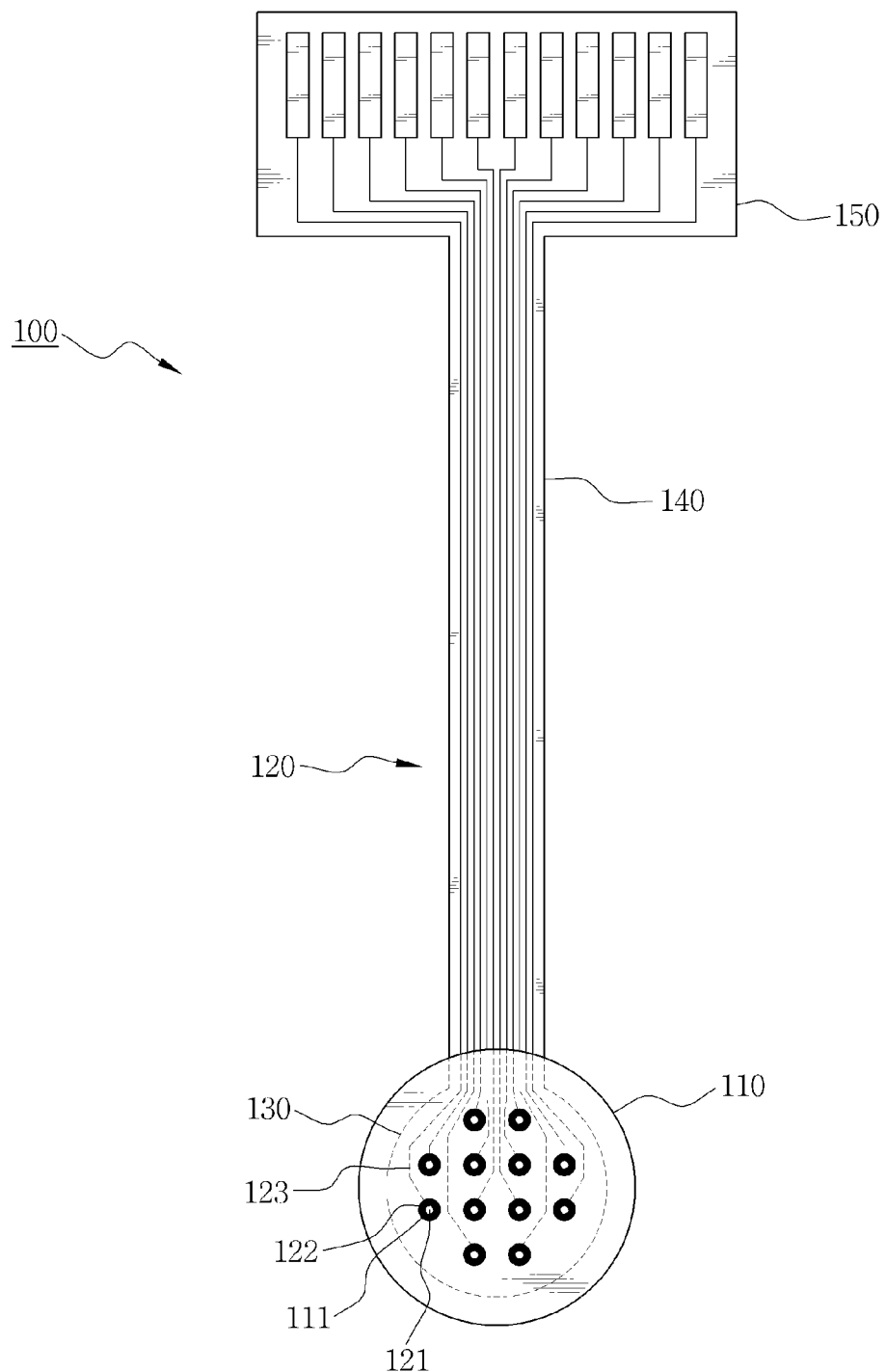

FIG. 1 is a perspective view showing a neural tube 100 according to an embodiment of the present disclosure, FIG. 2 is a perspective sectional view taken along the line A-A of FIG. 1, and FIG. 3 is a plane view showing the neural tube 100 of FIG. 1.

Referring to FIGS. 1 to 3, the neural tube 100 includes a cylindrical support 110 and a sieve electrode 120 buried in the support 110.

Figure 7:
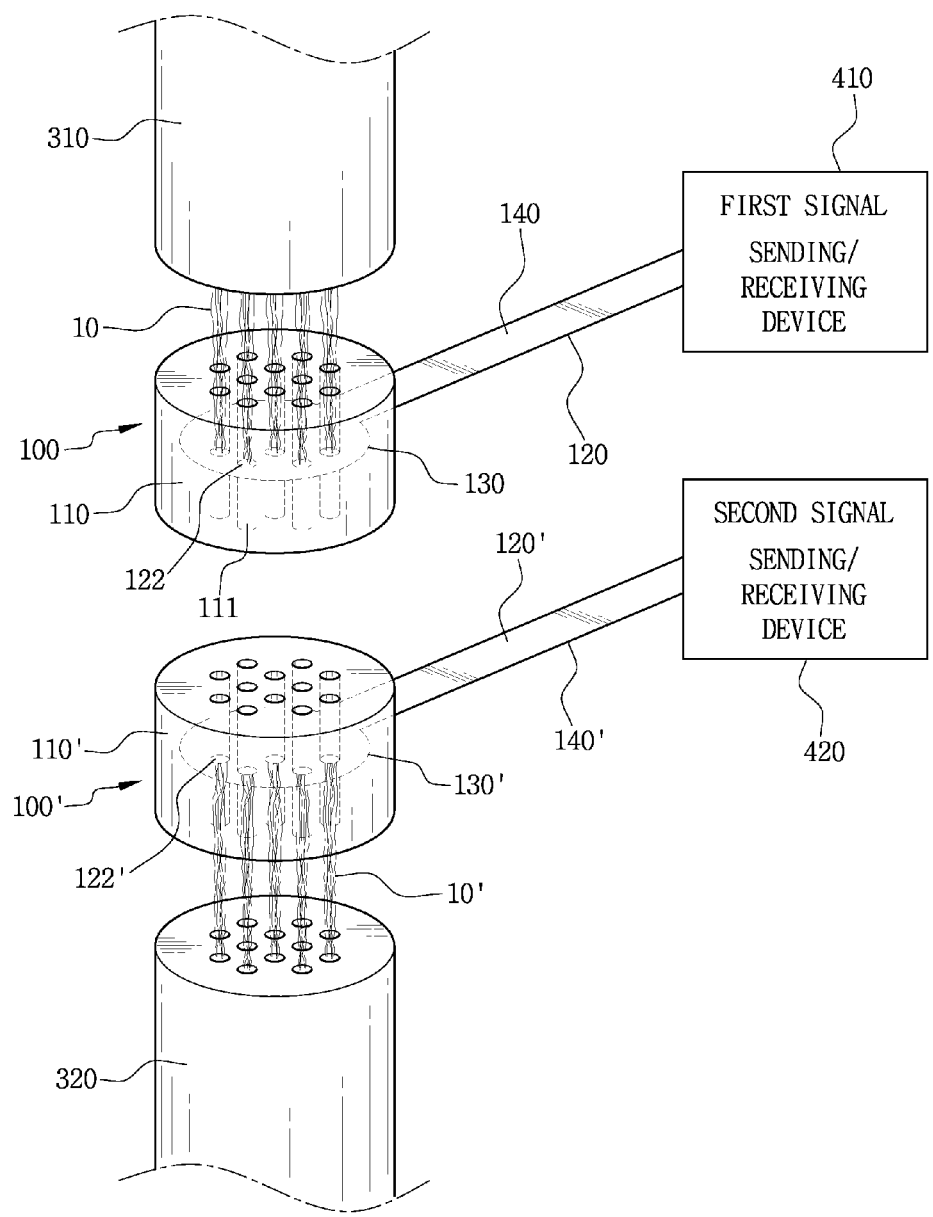
FIG. 7 is a diagram showing a neural signal detection device configured using the neural tube of FIG. 1.

The support 110 has a cylindrical body and is connected to a nerve injured by cutting (see FIG. 7). According to this embodiment, the support 110 is made of hydrogel and is formed by hardening molten hydrogel. The material of the support 110 is not limited to the above, and it should be understood that any bio-friendly material capable of forming a certain shape with a predetermined strength may be adopted as the support 110 of this embodiment.

The support 110 includes a plurality of channels 111 formed in a body thereof with a cavity shape in the length direction of the support 110. In FIGS. 1 and 2, the channels 111 and the sieve electrode 120 formed in the support 110 are shown with dotted lines for convenience.

The channel 111 lays a path along which a nerve cell grows from the terminal of a cut nerve. In this embodiment, the channel 111 contains a medicine which assists regeneration of a nerve cell and reduces an immune reaction.

The sieve electrode 120 of this embodiment has a thin plate shape, and a number of electrode holes 121 corresponding to the number of channels 111 are formed in the circular electrode body 130 to pass from the upper surface thereof to the lower surface thereof.

The sieve electrode 120 is made of soft polyimide material, and as well shown in FIG. 2, a circular electrode 122 is formed around the electrode holes 121, and a linear electrode 123 extending to an electrode connector 140 is electrically connected to the circular electrode 122.

As well shown in FIGS. 2 and 3, the electrode body 130 of the sieve electrode 120 is arranged perpendicular to the length direction of the channel 111. At this time, the electrode holes 121 are aligned with the channels 111 of the support 110 in a one-to-one relation. According to this embodiment, the center of the electrode hole 121 is located on the longitudinal axis of the channel 111. In other words, as shown in FIG. 3, the center of the electrode hole 121, which is a concentric circle, is coincided with the center of the channel 111.

According to this embodiment, the electrode hole 121 has a size smaller than the size of the channel 111. In this configuration, the circular electrode 122 formed around the electrode hole 121 is entirely or partially exposed in the channel 111 as a natural result.

Therefore, a nerve cell growing at the terminal of the injured nerve along the channel 111 may contact and be electrically connected to the circular electrode 122.

Meanwhile, as shown in FIGS. 1 to 3, the electrode connector 140 may extend from the electrode body 130 of the sieve electrode 120 to the outside of the support 110, and a pad 150 capable of being connected to sending/receiving devices 410, 420 is formed at the end of the electrode connector 140 (see FIG. 7).

A linear electrode 123 electrically connected to the circular electrode 122 extends at the electrode connector 140 and the pad 150, so that an electric signal from a nerve cell contacting the circular electrode 122 may be transferred to the outside.

The neural tube 100 of this embodiment may be made by molding the support 110 by hardening a molten solution of hydrogel to entirely surround at least the electrode body 130 of the sieve electrode 120. At this time, a jig of a suitable shape is used to form the channel 111 aligned with the electrode hole 122.

Figure 4:
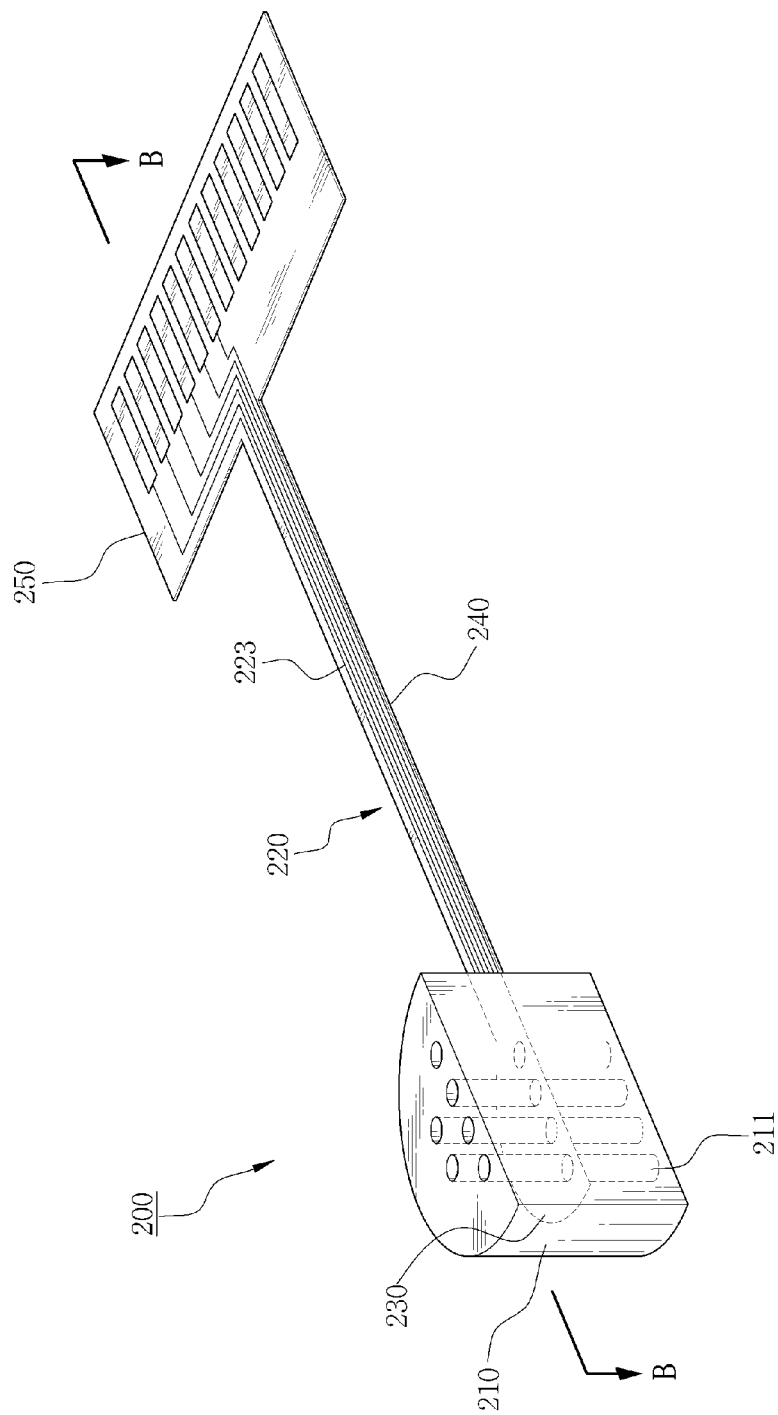
FIGS. 4 to 6 show a neural tube according to another embodiment of the present disclosure.
Figure 5:
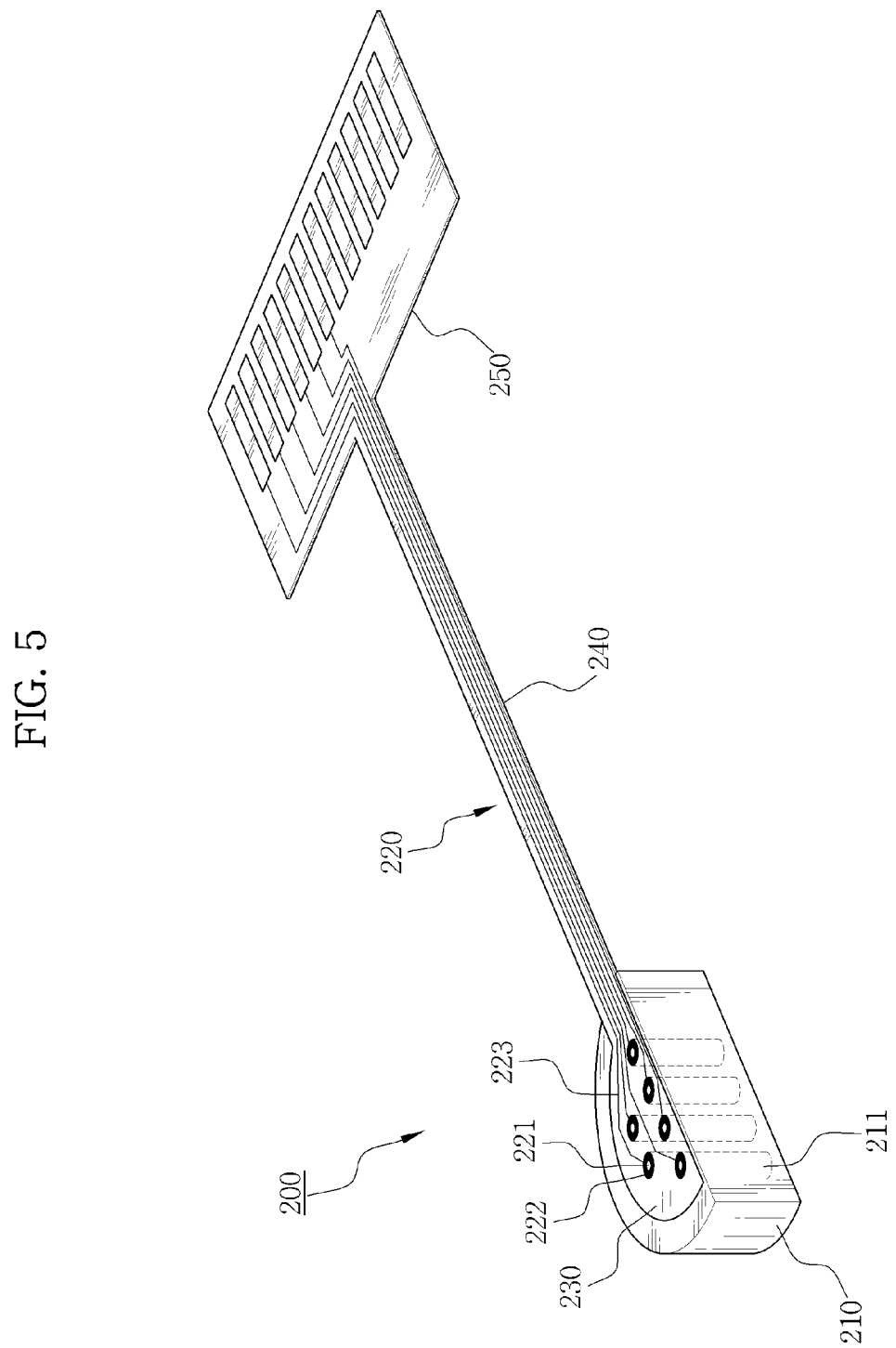
Figure 6:
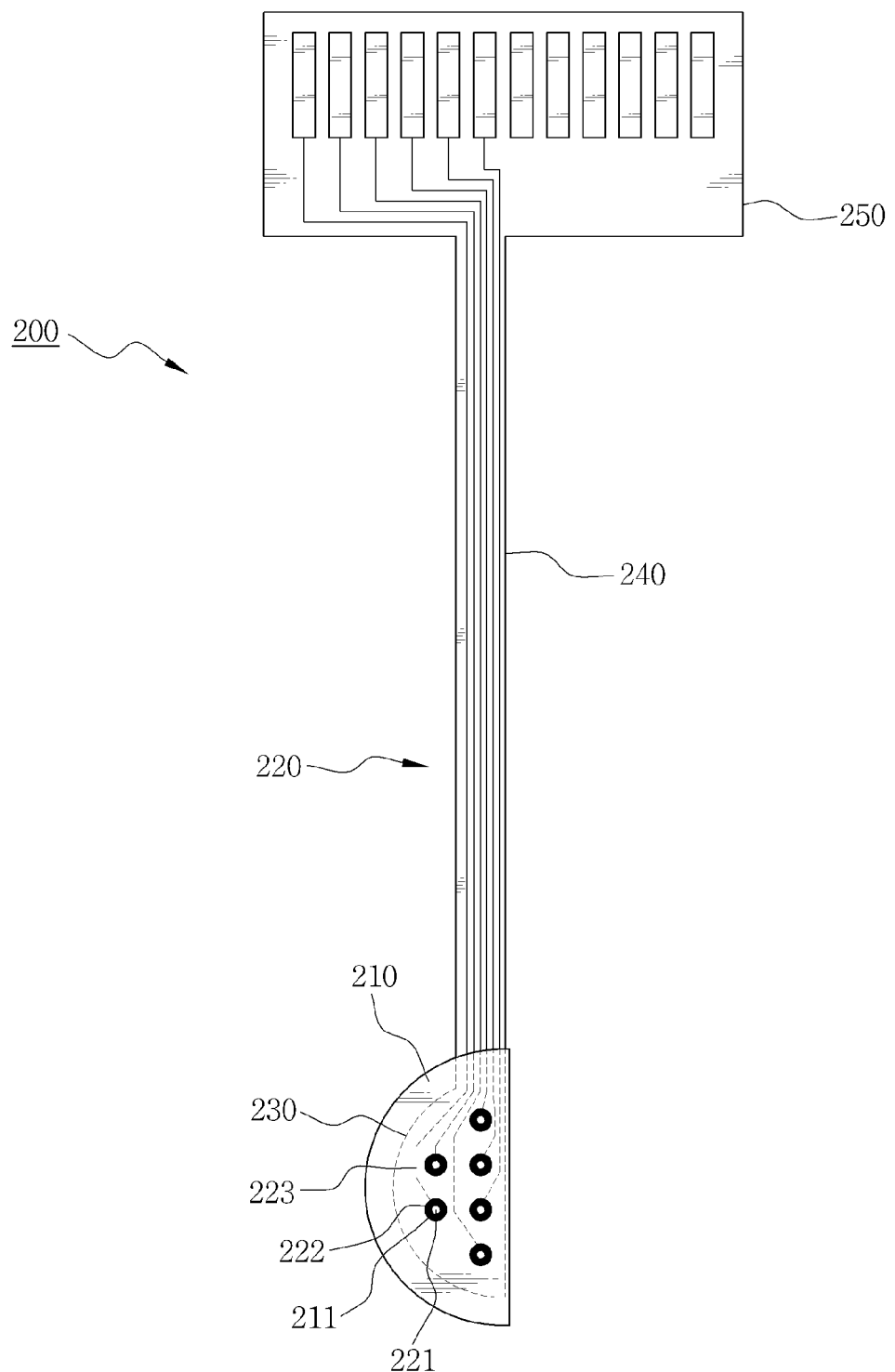

FIG. 4 is a perspective view showing a neural tube 200 according to another embodiment of the present disclosure, FIG. 5 is a perspective sectional view, taken along the line B-B of FIG. 4, and FIG. 6 is a plane view showing the neural tube 200 of FIG. 4.

The neural tube 200 of this embodiment has a support 210 with a substantially semicylindrical shape, and an electrode body 230 of a sieve electrode 220 has a semicircular shape corresponding thereto.

The neural tube 200 of this embodiment is substantially identical to the neural tube 100 of the former embodiment, except that the support 210 and the electrode body 230 of the sieve electrode 220 have a semicircular section.

Corresponding components of the neural tube 100 and the neural tube 200 are distinguished by endowing different hundreds digits, for example 100 and 200, while maintaining the tens digit and the units digit identically.

After cutting a spinal nerve of a mouse by half, for example, the neural tube 200 of this embodiment may be appropriately used for the terminal of the cut nerve. In other words, an electric signal of a normal nerve may be connected to the neural tube 200 and the transferred electric signal may be used for comparative experiments.

The use of the neural tube 200 is not limited just to experiments, but for example, the neural tube 200 may also be used for rehabilitation or treatment of patients by preparing and attaching a support 210 and a sieve electrode 220 in a shape corresponding to a cut portion of a patient whose nerve is partially cut.

FIG. 7 is a diagram showing a neural signal detection device using the neural tube 100 according to the embodiment of FIG. 1.

FIG. 7 shows a state in which a nerve is cut into an upstream nerve 310 and a downstream nerve 320. If cut nerve strands are spaced relatively distantly as described above, it is very difficult to regenerate nerve strands and connect them each other.

Therefore, according to this embodiment, a neural signal detection device for allowing a neural signal to be by-passed by using the neural tube without directly connecting nerves may be configured.

In detail, the neural tube 100 (first neural tube) is connected to an end of a cut upstream nerve 310. At this time, the support 110 is connected to the end of the nerve.

In a state where the neural tube 100 is connected, the upstream nerve 310 is regenerated so that the nerve cell 10 grows into each channel 111 of the neural tube 100.

Meanwhile, the pad 150 is connected to the first signal sending/receiving device 410, so that an electric signal transmitted from the circular electrode 122 may be sent to the first signal sending/receiving device 410 through the linear electrode 123.

If the nerve cell 10 grows in the channel 111 and contacts the circular electrode 122 so that an electric signal is detected, it may be easily understood that the nerve cell 10 is effectively regenerated by a medicine or the like.

Meanwhile, another neural tube 100' (second neural tube) is connected to an end of the cut downstream nerve 320. The second neural tube has the same configuration as the first neural tube.

In a state where the second neural tube 100' is connected, the downstream nerve 320 is regenerated so that the nerve cell 10' grows into each channel 111' of the second neural tube 100'.

Identically, the pad is connected to the second signal sending/receiving device 420, so that an electric signal transmitted from the circular electrode 122' may be sent to the second signal sending/receiving device 420 through the linear electrode 123'.

The first signal sending/receiving device 410 and the second signal sending/receiving device 420 may be connected in a wired or wireless manner to exchange signals.

If a signal from the brain is transferred to the circular electrode 122 of the first neural tube 100 through the upstream nerve 310, the signal is transferred to the first signal sending/receiving device 410.

The first signal sending/receiving device 410 sends the transferred neural signal to the second signal sending/receiving device 420, and the second signal sending/receiving device 420 sends the signal to the second neural tube 100', thereby to the downstream nerve 320.

It is known in the art that neural signals transferred through a single nerve strand may be classified based on functions (for example, into signals to be sent to the leg and signals to be sent to the hand). The neural signals transferred from the upstream nerve 310 are classified based on functions. The neural signals classified based on functions are transmitted to the second signal sending/receiving device 420 by the first signal sending/receiving device 410, and the second signal sending/receiving device 420 suitably classifies the signals again and transmits to the nerve cell 10'.

On the contrary, neural signals transferred from the downstream nerve 320 may be sent to the upstream nerve 310 through a route opposite to the above.

According to this configuration, even though cut nerve bundles are spaced relatively distantly, there is no burden of directly connecting the cut nerves.

In addition, since neural signals transferred from the upstream nerve may be classified based on functions and the classified signals may be distinguishably sent to each nerve cell of the downstream nerve in a suitable way, it is possible to prevent nerves from being erroneously connected and thus causing confusion in the nerve system.

According to this embodiment, even though the first neural tube 100 and the second neural tube 100' are separately formed independently, the present disclosure is not limited thereto. If the upstream nerve 310 and the downstream nerve 320 formed by cutting a nerve are disposed relatively closely, the supports of the first neural tube 100 and the second neural tube 100' may be integrally formed so that the cut nerve bundle may be fixed as a single strand.

In addition, according to this embodiment, since neural signals may be communicated wirelessly by the first signal sending/receiving device 410 and the second signal sending/receiving device 420, even though the first neural tube 100 is connected to the upstream nerve 310, the second neural tube 100' may not be directly connected to the downstream nerve 320 but the nerve may be directly connected to a final destination of the neural signal, for example the hand or the foot. In other words, a plurality of second neural tubes 100' and a plurality of second signal sending/receiving devices 420 connected thereto may be disposed at each point in a living body. This configuration may be very suitably used when, for example, the downstream nerve 320 is seriously damaged.

While the exemplary embodiments have been shown and described, it will be understood by those skilled in the art that various changes in form and details may be made thereto without departing from the spirit and scope of the present disclosure as defined by the appended claims.

What is claimed is:

1. A neural tube, comprising:
 a support configured to be connected to a terminal of an injured nerve; and
 a sieve electrode having an electrode hole formed in a body thereof and a circular electrode formed around the electrode hole,
 wherein the body of the sieve electrode is buried in the support,
 wherein a cavity-type channel is formed at the support to extend to the inside of the support,
 wherein the electrode hole is aligned with the channel, and
 wherein the channel is configured to allow a nerve cell to grow from the terminal of the injured nerve to the circular electrode.

2. The neural tube according to claim 1,
 wherein a plurality of electrode holes is formed in the sieve electrode,
 wherein a plurality of channels is formed in the support, and
 wherein the electrode holes are aligned with the channels in a one-to-one relation.

3. The neural tube according to claim 1,
 wherein the sieve electrode is disposed perpendicular to the length direction of the channel, and
 wherein the center of the electrode hole is located on a longitudinal axis of the channel.

4. The neural tube according to claim 1,
 wherein the support has a cylindrical shape.

5. The neural tube according to claim 1,
 wherein the support has a semicylindrical shape.

6. The neural tube according to claim 1,
 wherein the support is made of hydrogel.

7. The neural tube according to claim 1,
 wherein the channel contains a medicine for assisting regeneration of the nerve cell or reducing an immune reaction.

8. The neural tube according to claim 1,
 wherein the sieve electrode includes an electrode connector extending from a circular or semicircular electrode body to the outside of the support, and
 wherein a linear electrode electrically connected to the circular electrode is formed at the electrode connector.

* * * * *